United States Patent [19]
Ikai et al.

[11] Patent Number: 6,046,350
[45] Date of Patent: Apr. 4, 2000

[54] TERTIARY ALKYLSILANE

[75] Inventors: Keizo Ikai; Masaki Minami; Iwane Shiozaki, all of Yokohama, Japan

[73] Assignee: Nippon Oil Co., Ltd., Tokyo, Japan

[21] Appl. No.: 09/208,382

[22] Filed: Dec. 9, 1998

[30] Foreign Application Priority Data

Dec. 11, 1997 [JP] Japan .................................. 9-362128

[51] Int. Cl.$^7$ ........................................................ C07F 7/08
[52] U.S. Cl. ............................................................ 556/487
[58] Field of Search ............................................... 556/487

[56] References Cited

PUBLICATIONS

Akira Watanabe, et al., "Electrical and Optical Properties of Heat–treated Silicon Network Polymers", The Chemical Society of Japan, Chemistry Letters (1991), pp. 1101–1104.

*Primary Examiner*—Paul F. Shaver
*Attorney, Agent, or Firm*—Akin, Gump, Strauss, Hauer & Feld, L.L.P.

[57] ABSTRACT

A novel tertiary alkylsilane is disclosed, which is useful as a variety of starting materials such as for photoreactive materials including semiconductor materials, insulative materials and photoresists, polymerization initiators and silicone-based ceramics precursors and is contributive to the safe and efficient production of high grade semiconductors.

4 Claims, No Drawings

TERTIARY ALKYLSILANE

BACKGROUND OF THE INVENTION

1. Field of the Invention

This invention relates to a novel tertiary alkylsilane, more particularly to such a tertiary alkylsilane which is used as a starting material (monomer) for CVD (chemical vapor deposition) film forming and becomes more effective by being polymerized to be made polysilane which can be widely used as starting materials for photoreactive materials such as silicone semiconductor materials, silicone electro-conductive materials, silicone carbide semiconductor materials, silicone nitride semiconductive materials, silicone oxide insulative materials, photoconductive material and photoresists, polymerization initiators and precursors of silicone-based ceramics.

2. Description of the Related Art

Recently, the semiconductor industry has been burdened with enormously increased facility cost because steel gas cylinders for storing a material need to be installed far away from an operation site so as to ensure safety operation. The present situation is that in the production of a high quality semiconductor with use of the existing material, 90 percent thereof is discarded, resulting inefficient productivity.

In recent years, an attempt has been made to use polysilanes for an electro- or photo-conductive material. For instance, a high electro-conductive material can be produced by doping a straight-chain-like polymethylphenylsilane with $AsF_5$.

Another attempt has been made on the production of an electro- or photo-conductive material by thermal decomposition of polysilane in which instance according to the report made in Chem. Lett., 1101 published in 1991, polyphenylsilane having a molecular structure of networks is formed into a film and then thermally decomposed in a vacuum thereby obtaining an SiC film and furthermore the thermal decomposition at a temperature of 600° C. results in the formation of a semiconductive film having an Eg. opt value of 1.1 eV.

However, polyphenylsilane is not suitable for a material used in the production of an photoconductive material because its hydrocarbon substituent is low in elimination properties in the thermal decomposition process, causing that a large amount of hydrocarbon remains in the resulting material after the thermal decomposition.

SUMMARY OF THE INVENTION

A novel tertiary alkylsilane has now been found by the present inventors as a result of an extensive research with the above-mentioned background.

A tertiary alkylsilane according to the invention is represented by the formula

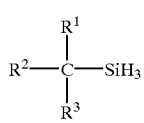
(1)

wherein $R^1$, $R^2$ and $R^3$ each are a $C_1$–$C_4$ alkyl group, provided that if either $R^1$ or $R^3$ is a methyl group, the other is not a methyl group, and may be cross-linked to each other.

DETAILED DESCRIPTION OF THE INVENTION

The inventive tertiary alkylsilane is represented by the formula

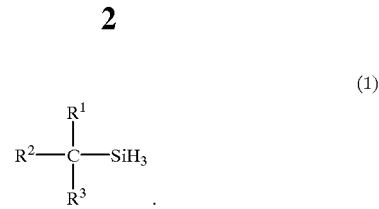

In the above formula, $R^1$–$R^3$ each are a $C_1$–$C_4$ alkyl group, provided that both $R^1$ and $R^3$ are not a methyl group at the same time, and may be cross-linked to each other. Specific examples of such an alkyl group include methyl, ethyl, n-propyl, n-butyl, iso-propyl, sec-butyl, iso-butyl and tert-butyl groups.

If $R^1$ through $R^3$ are cross-linked to each other, the group of the linked portion may be a $C_1$–$C_4$ divalent hydrocarbon group such as methylene, ethylene, trimethylene, tetramethylene, propylene and butylene groups.

Specific examples of tertiary alkylsilane of formula (1) are
2-methyl-2-butylsilane, 2-methyl-2-pentylsilane, 2-methyl-2-hexylsilane,
3-methyl-3-pentylsilane, 3-ethyl-3-pentylsilane, 1,1,2-trimethylpropylsilane (2, 3-dimethyl-2-butylsilane)
3,4dimethyl-3-hexylsilane, 2,3,4-trimethyl-3-pentylsilane,
2,3,4-trimethyl-2-pentylsilane, 2,3,4,5-tetramethyl-3-hexylsilane,
2,3,3-trimethyl-2-butylsilane, 2,2,3,5,5-pentamethyl-3-hexylsilane,
1-methylcyclobutylsilane, 1,2-dimethylcyclobutylsilane,
1-methylcyclopentylsilane, 1,2-dimethylcyclopentylsilane,
1-methylcyclohexylsilane, 1,2-dimethylcyclohexylsilane,
1-bicyclo[2.2.1]heptylsilane, 1-bicyclo[2.2.2]octylsilane,
1-bicyclo[3.2.1]octylsilane, 2-methyl-1-bicyclo[3.2.1]octylsilane,
1-bicyclo[3.2.2]nonylsilane, 2-methyl-1-bicyclo[3.2.2]nonylsilane,
1-bicyclo[4.2.2]decylsilane, 2-methyl-1-bycyclo[4.2.2]decylsilane,
1-adamantylsilane and 1-homoadamantylsilane.

The inventive tertiary alkylsilane may be produced by a variety of conventional known synthesizing methods and thus the production method is not particularly restricted. Two typical methods are herein exemplified as Methods A and B.

A first method (Method A) is conducted by reacting an olefin substituted at the 4-position and silane (monosilane) in the presence of a radical initiator so as to hydrosilylating the olefin, as indicated by the formula

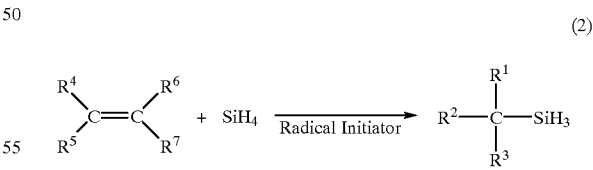
(2)

wherein $R^1$, $R^2$ and $R^3$ each are the same as those exemplified with regard to formula (I) and $R^4$, $R^5$, $R^6$ and $R^7$ each are a $C_1$–$C_4$ alkyl group and may be cross-linked to each other.

Although no particular limitation is imposed upon the radical initiator used in this method, there may generally used 1,1'-azobis(isobutylonitrile) (AIBN), 1,1'-azobis(cyclohexane-1-carbonitrile) (ACHN), 2,2'-azobis(2-methylbutylonitrile), 2,2'-azobis(2,4-dimethylvaleronitrile) and 2,2'-azobis(2-methylpropane).

Eligibles for the 4-position-substituted olefins are 3-methyl-2-pentene,
3-ethyl-2-pentene, 2,3-dimethyl-2-butene, 3,4-dimethyl-3-hexene,
2,3,4-trimethyl-2-pentene, 2,3,5-trimethyl-2-hexene,
2,3,4,5-tetramethyl-2-hexene, 2,3,4,5-tetramethyl-3-hexene,
2,2,3,4,5,5-hexamethyl-3-hexene, 1,2-dimethylcyclobutene,
1,2-dimethylcyclopentene, 1,2-dimethylcyclohexene,
2-methylbicyclo[3.2.1]octene, 2-methylbicyclo[3.2.2]nonene and
2-methylbicyclo[4.2.2]decene.

The reaction indicated by formula (2) may be carried out in any suitable manner. Generally, there is employed a method in which the 4-position-substituted olefin is reacted with a silane gas in an autoclave. The reaction is conducted normally at a temperature of 80–230° C., preferably 100–200° C. for a period of from 30 minutes to 5 days, preferably one hour to 100 hours.

The molar ratio of the 4-position-substitued olefin to the silane gas may be selected from the range of 0.1 to 5.0, preferably 0.3 to 3.0.

Although the amount of the radical initiator is also selective, the molar ratio of the radical initiator to the 4-position-substitued olefin is within the range of 0.05to 1.0.

The intended product can be easily recovered by distilling the reaction product.

A second method (Method B) is to reduce tertiary alkyltrihalogenosilane having a silicone atom bonded with 3 halogen atoms, as indicated by the formula

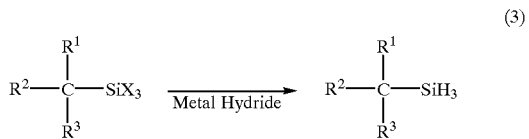

(3)

wherein $R^1$, $R^2$ and $R^3$ each are the same as those already exemplified with regard to formula (1) and X is a halogen atom.

Preferred halogen atoms are fluorine, chlorine, bromine and iodine.

Specific examples of tertiary alkyltrihalogenosilane are
2-methyl-2-butyltrichlorosilane, 2-methyl-2-pentyltrichlorosilane,
2-methyl-2-hexyltrichlorosilane, 3-methyl-3-pentyltrichlorosilane,
3-ethyl-3-pentyltrichlorosilane, 2,3-dimethyl-2-butyltrichlorosilane,
3,4-dimethyl-3-hexyltrichlorosilane, 2,3,4-trimethyl-3-pentyltrichlorosilane,
2,3,4-trimethyl-2-pentyltrichlorosilane,
2,3,4,5-tetramethyl-3-hexyltrichlorosilane,
2,3,3-trimethyl-2-butyltrichlorosilane,
2,2,3,5,5-pentamethyl-3-hexyltrichlorosilane,
1-methylcyclobutyltrichlorosilane, 1,2-dimethylcyclobutyltrichlorosilane,
1-methylcyclopentyltrichlorosilane, 1 2-dimethylcyclopentyltrichlorosilane,
1-methylcyclohexyltrichlorosilane, 1,2-dimethylcyclohexyltrichlorosilane,
1-bicyclo[2.2.1]heptyltrichlorosilane, 1-bicyclo[2.2.2]octyltrichlorosilane,
1-bicyclo[3.2.1]octyltrichlorosilane,
2-methyl-1-bicyclo[3.2.1]octyltrichlorosilane,
1-bicyclo[3.2.2]nonyltrichlorosilane,
2-methyl-1-bicyclo[3.2.2]nonyltrichlorosilane,
1-bicyclo[4.2.2]decyltrichlorosilane,
2-methyl-1-bicyclo[4.2.2]decyltrichlorosilane,
1-adamanthyltrichlorosilane and
1-homoadamanthyltrichlorosilane.

Eligible metal hydrides for this second reaction are lithium hydride, sodium hydride, sodium borohydride and aluminum borohydride.

Although there is no particular limitation imposed upon the method for conducting the reaction of formula (3), there is generally employed a method in which alkyltrihalogenosilane is reacted with the metal hydride in an ethereal solvent such as diethylether, dibutylether and tetrahydrofuran or in a hydrocarbonous solvent such as benzenetoluene and hexane. The reaction temperature is within the range of usually −20 to 100° C., preferably 0 to 80° C. The time required for completing the reaction is selected depending on the reaction scale and the size of a reaction vessel but is within the range of usually 5 minutes to one day, preferably 10 minutes to 6 hours.

Although there is no particular limitation imposed on the amount of the metal hydride, the molar ratio of the metal hydride to alkyltrihalogenosilane is within the range of 0.5 to 5.0, preferably 0.7 to 3.0.

The intended reaction product can be recovered by deactivating the metal hydride remaining in the reaction mixture with use of water or an alcohol and distilling after the byproduct salt being removed by filtration or water-washing.

The tertiary alkyltrihalogenosilane used as a stating material for Method B may be produce by any suitable method. Although such a method is not particularly limited, there are two methods, for example.

A first method (Method B-1) is conducted by reacting an organic metal compound with a tetrahalogenated silicone as indicated by the formula

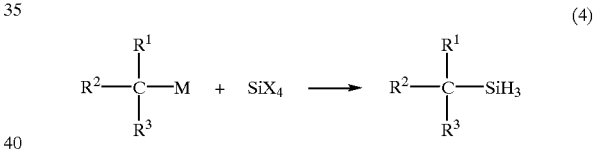

(4)

wherein $R^1$, $R^2$ and $R^3$ each are the same as those already exemplified with regard to formula (1).

Eligible organic metal compounds for this method are alkyllithium such as
2-methyl-2-butyllithium, 2-methyl-2-pentyllithium, 2-methyl-2-hexyllithium,
3-methyl-3-pentyllithium, 3-ethyl-3-pentyllithium, 2,3-dimethyl-2-butyllithium,
3,4-dimethyl-3-hexyllithium, 2,3,4-trimethyl-3-pentyllithium,
2,3,4-trimethyl-2-pentyllithium, 2,3,4,5-tetramethyl-3-hexyllithium,
2,3,3-trimethyl-2-butyllithium, 2,2,3,5,5-pentamethyl-3-hexyllithium,
1-methylcyclobutyllithium, 1,2-dimethylbutyllithium, 1-methylcyclopentyllithium,
1,2-dimethylcyclopentyllithium, 1-methylcyclohexyllithium,
1,2-dimethylhexyllithium, 1-bicyclo[2.2.1]heptyllithium,
1-bicyclo[2.2.2]octyllithium, 1-bicyclo[3.2.1]octyllithium,
2-methyl-1-bicyclo[3.2.1]octyllithium, 1-bicyclo[3.2.2]nonyllithium,
2-methyl-1-bicyclo[3.2.2]nonyllithium, 1-bicyclo[4.2.2]decyllithium,
2-methyl-1-bicyclo[4.2.2]decyllithium, 1-adamantyllithium and 1-homoadamantyllithium; and alkylmagnesiumbromide such as
2-methyl-2-butylmagnesiumbromide, 2-methyl-2-pentylmagnesiumbromide,
2-methyl-2-hexylmagnesiumbromide, 3-methyl-3-pentylmagnesiumbromide,
3-ethyl-3-pentylmagnesiumbromide, 2,3-dimethyl-2-butylmagnesiumbromide,
3,4-diemthyl-3-hexylmagnesiumbromide,
2,3,4-trimethyl-3-pentylmagnesiumbromide,
2,3,4-trimethyl-2-pentylmagnesiumbromide,
2,3,4,5-tetramethyl-3-hexylmagnesiumbromide,
2,3,3-trimethyl-2-butylmagnesiumbromide,
2,2,3,5,5-pentamethyl-3-hexylmagnesiumbromide,
1-methylcyclobutylmagnesiumbromide,
1,2-dimethylcyclobutylmagnesiumbromide,
1-methylcyclopentylmagnesiumbromide,
1,2-dimethylcyclopentylmagnesiumbromide,
1-methylcyclohexylmagnesiumbromide,
1,2-dimethylcyclohexylmagnesiumbromide,
1-bicyclo[2.2.1]heptylmagnesiumbromide,
1-bicyclo[2.2.2]octylmagnesiumbromide,
1-bicyclo[3.2.1]octylmagnesiumbromide,
2-methyl-1-bicyclo[3.2.1]octylmagnesiumbromide,
1-bicyclo[3.2.2]nonylmagnesiumbromide,
2-methyl-1-bicyclo[3.2.2]nonylmagnesiumbromide,
1-bicyclo[4.2.2]decymalmagnesiumbromide,
2-methyl-1-bicyclo[4.2.2]decymalmagnesiumbromide,
1-adamantylmagnesiumbromide and 1-homoadamantylmagnesiumbromide.

These organic metal compounds can be easily obtained by reacting halogenated cycloalkan with lithium or magnesium in an ethereal solvent such as diethylether and tetrahydrofuran.

The tetrahalogenated silane to be reacted with the organic metal compound may be selected arbitrary but preferred is tetrachlorosilane.

A second method (B-2) for producing tertiary alkyltrihalogenosilane is conducted by reacting an olefin substituted at the 4-position and trihalogenosilane in the presence of a radical initiator, as indicated by the formula

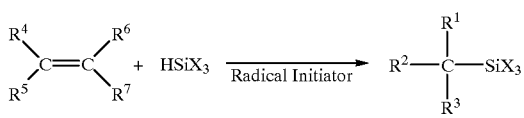

(5)

wherein $R^1$, $R^2$ and $R^3$ each are the same as those already described with regard to formula (1) and $R^4$, $R^5$, $R^6$ and $R^7$ each are a $C_1$–$C_4$ alkyl group and may be cross-linked to each other.

Although no particular limitation is imposed on the radical initiator used for this method, there may be generally used 1,1'-azobis(isobutylonitrile) (AIBN), 1,1'-azobis(cyclohexane-1-carbonitrile) (ACHN), 2,2'-azobis(2-methylbutylonitrile), 2,2'-azobis(2,4-dimethylvaleronitrile) and 2,2'-azobis(2-methylpropane).

Eligible 4-posistion-substituted olefins are 3-methyl-2-pentene, 3-ethyl-2-pentene, 2,3-dimethyl-2-butene, 3,4-dimethyl-3-hexene, 2,3,4-trimethyl-2-pentene, 2,3,5-trimethyl-2-hexene, 2,3,4,5-tetramethyl-2-hexene, 2,3,4,5-tetramethyl-3-hexene, 2,2,3,4,5,5-hexamethyl-3-hexene, 1,2-dimethylcyclobutene, 1,2-dimethylcyclopentene, 1,2-dimethylcyclohexene, 2-methylbicyclo[3.2.1]octene, 2-methylbicyclo[3.2.2]nonene and 2-methylbicyclo[4.2.2]decene.

The trihalogenated silane to be reacted with the 4-position-substituted olefin may be selected arbitrary but preferred is trichlorosilane.

The reaction indicated by formula (5) may be conducted by any suitable method but there may be generally employed a method in which the 4-posistion substituted olefin is reacted with trihalogenated silane in an autoclave. The reaction temperature is within the range of usually 80 to 230° C., preferably 100 to 200° C. The time required for completing the reaction is selected depending on the reaction scale and the size of a reaction vessel but is within the range of usually 30 minutes to 5 days, preferably one hour to 100 hours.

The molar ratio of the 4-position-substituted olefin to trihalogentaed silane is selected arbitrary but is usually within the range of 0.1 to 5.0, preferably 0.3 to 3.0.

Although the amount of the radical initiator is also selected arbitrary, the molar ratio of the radical initiator to the 4-position substituted olefin is usually within the range of 0.05 to 1.0.

The intended product can be easily recovered by distilling the reaction mixture.

The inventive tertiary alkylsilane represented by formula (1) is useful as a variety of starting materials such as for photoreactive materials including semiconductor materials, insulative materials and photoresists, polymerization initiators and silicone-based ceramics precursors and is contributive to the safe and efficient production of high quality semiconductors.

The tertiary alkylsilane according to the invention is also contributive to the production of polysilane in the form of networks having a carbon substituent group excelled in elimination properties upon thermal decomposition in a vacuum or under an atmosphere of hydrogen, nitrogen or argon.

EXAMPLES

The following examples are presented to illustrate specific embodiments of the present invention and should not be interpreted as limitations upon the scope of the invention.

Example 1

A two-liter autoclave (Husteroy) equipped with a stirrer was charged in a nitrogen atmosphere with 177 grams (2.10 mols) of 2,3-dimethyl-2-butene, 562 grams (4.16 mols) of trichlorosilane and 100 grams (0.41 mol) of 1,1'-azobiscyclohexanecarbonitrile. The mixture was stirred and heated at a temperature of 130° C. for 3 hours. The resulting reaction liquid was purified by distillation thereby obtaining 406 grams of 1,1,2-trimethylpropyltrichlorosilane (yield: 88%).

Then, a three-liter four-necked flask equipped with a stirrer, a reflux cooling tube and a dropping funnel was charged in a nitrogen atmosphere with 150 grams (6.25 mols) of sodium hydride and 2 liters of hexamethylphosphoricamide and then added with droplets of 406 grams (1.85 mol) of 1,1,2-trimethylpropyltrichlorosilane obtained above at room temperature with stirring over 3 hours. After completion of the dropwise addition, the mixture was stirred for another one hour and the precipitate was captured in a trap kept at a temperature of −78° C. under reduced pressure in an oil pump. The precipitate thus captured was purified by distillation thereby obtaining 129 grams (yield: 60%) of 1,1,2-trimethylpropylsilane. The boiling point and structure of the resulting product was examined and the elemental analysis therefor was conducted. The results were as follows:

Boiling Point: 98° C. (atmospheric pressure)

$^1$HNMR Spectrum (CDCl3)δ: 0.93(d, 6H), 1.02(s, 6H), 1.56(m, 1H) 3.46(s, 3H)

Elemental Analysis ($C_6H_{16}Si$): Calc'd: C 61.98, H 13.87, Si 24.15 Found: C 62.05, H 14.09, Si 23.86

Example 2

A two-liter four-necked flask equipped with a stirrer, a reflux cooling tube and a dropping funnel was charged in a nitrogen atmosphere with 85 grams (0.5 mol) of tetrachlorosilane and 500 ml of diethylether and then added with the droplets of 500 ml of 1,1-dimethylpropyllithium (1.0 M diethylether solution) as being stirred and cooled with ice over 2 hours. After completion of the addition, stirring was continued for another one hour at room temperature. The resulting mixture was filtered out in a nitrogen atmosphere and then purified by distillation thereby obtaining 36 grams (yield : 35%) of 1,1-dimethylpropyltrichlorosilane.

Then, a 0.5-liter four-necked flask equipped with a stirrer, a reflux cooling tube and a dropping funnel was charged in a nitrogen atmosphere with 15 grams (0.39 mol) of lithiumaluminum hydride and 300 ml of diethylene glycol dimethylether and then added with the droplets of 36 grams (0.18 mol) of 1,1-dimethylpropyltrichlorosilane at room temperature over one hour with stirring. After the completion of the addition, stirring was continued for another one hour. The mixture was then heated to 40° C. under reduced pressure in an oil pump and the precipitate was captured in a trap kept at a temperature of −78° C. The precipitate thus captured was purified by distillation thereby obtaining 9.8 grams (yield: 53%) of 1,1-dimethylpropylsilane. The resulting product was examined for boiling point and structure and identified by elemental analysis. The results were given below.

Boiling Point: 63° C. (atmospheric pressure)

$^1$HNMR Spectrum (CDCl3)δ: 0.98(t, 3H), 1.05(s, 6H), 1.50(q, 2H) 3.40(s, 3H)

Elemental Analysis ($C_6H_{16}Si$): Calc'd: C 58.73, H 13.80, Si 27.47 Found: C58.69, H 14.12, Si 27.19

Example 3

A one-liter autoclave equipped with a stirrer was charged in a nitrogen atmosphere with 7.0 grams (0.07 mol) of 1,2-dimethylcyclopentene, 3.4 grams (0.014 mol) of 1,1'-azobiscyclohexanecarbonitrile and 20 ml of hexane. 4.5 gram silane gas was introduced into the autoclave and the mixture was heated at 130° C. for 3 hours. After removal of the unreacted silane gas, the reaction mixture was purified by distillation thereby obtaining 1.2 gram (yield: 13%) of 1,2-dimethylcyclopentylsilane. The resulting product was examined for boiling point and structure and identified by elemental analysis. The results were given below.

Boiling Point: 120–145° C. (atmospheric pressure)

$^1$HNMR Spectrum (CDCl3)δ: 0.9–2.5(m, 13H), 3.5(s, 3H)

Elemental Analysis ($C_6H_{16}Si$): Calc'd: C 65.54, H 12.57, Si 21.89 Found: C 65.68, H 12.77, Si 21.55

As described above, the present invention provides tertiary alkylsilane which finds an extensive use for a variety of starting materials such as photoreactive materials including semiconductor materials, insulative materials, and phtoresists, polymerization initiators and precursors of silicone-carbide based ceramics and are conducive to the safety and efficient production of high grade semiconductors.

What is claimed is:

1. A tertiary alkylsilane represented by the formula

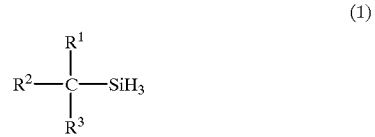

(1)

wherein $R^1$, $R^2$ and $R^3$ each are a $C_1$–$C_4$ alkyl group and may be cross-linked to each other, provided that $R^1$, $R^2$ and $R^3$ are not all methyl groups at the same time.

2. Tertiary alkylsilane according to claim 1 comprising 1,1,2-trimethylpropylsilane.

3. Tertiary alkylsilane according to claim 1 comprising 1,1-dimethylpropylsilane.

4. Tertiary alkylsilane according to claim 1 comprising 1,2-dimethylcyclopentylsilane.

* * * * *